United States Patent
Chang et al.

(10) Patent No.: US 7,504,538 B2
(45) Date of Patent: Mar. 17, 2009

(54) AMIDE OR THIOAMIDE DERIVATIVES AND THEIR USE IN THE TREATMENT OF PAIN

(75) Inventors: Chia-Ping Chang, San Diego, CA (US); Jacek Stalewski, San Diego, CA (US); Piere J-M. Riviere, San Diego, CA (US); Kazimierz A. Wisniewski, San Diego, CA (US); Claudio D. Schteingart, San Diego, CA (US)

(73) Assignee: Cara Therapeutics, Inc., Tarrytown, NY (US)

( * ) Notice: Subject to any disclaimer, the term of this patent is extended or adjusted under 35 U.S.C. 154(b) by 0 days.

(21) Appl. No.: 10/575,976

(22) PCT Filed: Oct. 14, 2004

(86) PCT No.: PCT/US2004/033698

§ 371 (c)(1),
(2), (4) Date: Feb. 23, 2007

(87) PCT Pub. No.: WO2005/037798

PCT Pub. Date: Apr. 28, 2005

(65) Prior Publication Data

US 2007/0197653 A1 Aug. 23, 2007

Related U.S. Application Data

(60) Provisional application No. 60/511,577, filed on Oct. 16, 2003.

(51) Int. Cl.
C07C 275/00 (2006.01)
(52) U.S. Cl. ............................... 564/48; 564/47; 564/57
(58) Field of Classification Search ........................ None
See application file for complete search history.

(56) References Cited

U.S. PATENT DOCUMENTS

| 2,447,587 A | 8/1948 | Martin et al. |
| 5,516,795 A | 5/1996 | Dellaria et al. |

FOREIGN PATENT DOCUMENTS

| DE | 2 005 326 | | 8/1971 |
| DE | 33 29 628 | | 3/1984 |
| GB | 2126224 | * | 3/1984 |
| WO | 02/085866 | | 10/2002 |

OTHER PUBLICATIONS

Online CAS citation 100:210422 for GB 2126224 [retrieved Mar. 13, 2008]from STN; Columbus, OH, USA.*
Deck et al., Journal of Heterocyclic Chemistry (2000), 37(4), 675-680; online CAS citation 134:17456 [retrieved Mar. 13, 2008] from STN; Columbus, OH, USA.*
Lee et al., Heterocycles (1994), 38(12), 2605-14;CAS citation 122:133069 [retrieved Mar. 13, 2008] from STN; Columbus, OH, USA.*
Machacek et al., Collection of Czechoslovak Chemical Communications (1987), 52(1), 140-55 ;online CAS citation 107:197246 [retrieved Mar. 13, 2008] from STN; Columbus, OH, USA.*
CAS online citation 136:263169 [retrieved Oct. 18, 2008] from STN; Columbus, OH, USA.*
Database Beilstein: XP002319731: Database Accession No. BRN 8702792 Abstract: Deck et al., 2000, J. Heterocycl. Chem., 37(4): 675-680.
Database Beilstein: XP002319732: Database Accession No. BRN 2808453 Abstract: Elmore, 1961, J. Chem. Soc., 3161-3162.
Database Beilstein: XP002319733: Database Accession No. BRN 2993980 Abstract: Suminov, 1967, Moscow Univ. Chem. Bull., 22(1): 57-75.
Database Beilstein: XP002319734: Database Accession No. BRN 7033473 Abstract: Mizrakh et al., 1993, Russ. J. Gen. Chem., 63(3.2): 497-498.
Database Beilstein: XP002319735: Database Accession No. BRN 4450540, 4435773 Abstract: Machacek et al., 1987, Collect. Czech. Chem. Commun., 52(1): 140-155.
Database Beilstein: XP002319736: Database Accession No. BRN 7218655, 7218660 Abstract: Lee et al., 1994, Heterocycles, 38(12): 2605-2614.
Database Beilstein: XP002319737: Database Accession No. BRN 2669014 Abstract: Ugi et al., 1961, Chem. Ber., 94: 2814.
Boger et al., "Vancomycin and Ristocetin Models: Synthesis via the Ullman Macrocyclization Reaction", 1993, J. Org. Chem., 58(6): 1425-1433.

* cited by examiner

*Primary Examiner*—Karl J Puttlitz
(74) *Attorney, Agent, or Firm*—Pillsbury Winthrop Shaw Pittman LLP

(57) ABSTRACT

The present invention relates to novel compounds, pharmaceutical compositions comprising the same, use of said compounds for the manufacture of a medicament for treatment of pain and disorders related thereto as well as a method for treatment of pain and disorders related thereto, wherein said compounds are administered. The compounds are represented by the general formula (I), as further defined in the specification.

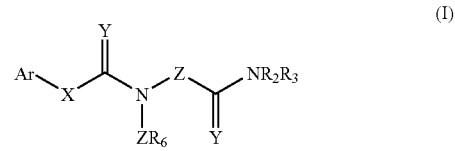

20 Claims, No Drawings

AMIDE OR THIOAMIDE DERIVATIVES AND THEIR USE IN THE TREATMENT OF PAIN

This application claims priority to both U.S. Application Ser. No. 60/511,577, filed Oct. 16, 2003, entitled "NOVEL COMPOUNDS" and International Application No. PCT/US2004/033698, filed Oct. 14, 2004, entitled "AMIDE OR THIOMIDE DERIVATIVES AND THEIR USE IN THE TREATMENT OF PAIN," and the disclosures of both said priority applications are hereby incorporated herein by reference in their entirety and for all purposes.

FIELD OF THE INVENTION

The present invention relates to novel compounds, pharmaceutical compositions comprising the same, use of said compounds for the manufacture of a medicament for treatment of pain and disorders related thereto as well as a method for treatment of pain and disorders related thereto, wherein said compounds are administered.

BACKGROUND

The preparations from the plant *Cannabis sativa* (marijuana) are well known to have therapeutic effect against various diseases. Their active component, cannabinoids, exerts a wide spectrum of central and peripheral actions, such as analgesia, anti-convulsion, anti-inflammation and alleviation of both intraocular pressure and emesis. Cannabinoids have also shown efficacy as immune modulators in animal models of neurological conditions, such as experimental allergic encephalomyelitis (EAE) and neuritis. Since cannabinoids furthermore have the ability to inhibit the growth of various types of cancer cells in culture, as well as to induce the regression of gliomas in laboratory animals, they are also potential anti-tumor agents.

The most active component of marijuana, $\Delta^9$-tetrahydrocannabinol (THC), is a prescribed drug e.g. for the relief of nausea associated with cancer chemotherapy. THC research has lead to the discovery of cannabinoid receptors. It has recently been hypothesised that lipid derivatives, so-called endocannabinoids, represent the naturally occurring endogenous ligands for these receptors.

The effects of THC and the major endocannabinoids, anandamide and 2-arachidonyl glycerol, are mediated by the activation of specific G-protein coupled receptors. To date two different cannabinoid receptors have been cloned from mammalian tissues, and these are denoted CB1 and CB2. The central and most of the peripheral effects of cannabinoids are the result of CB1 activation. This receptor is abundant in the central nervous system where it mediates cannabinoid psychoactivity. CB1 is also present in peripheral nerve terminals and in non-neuronal sites, such as the testis, uterus, eyes, vascular endothelium and immune cells. CB2 is predominantly present in peripheral tissues that are associated with immune functions, i.e. spleen, tonsils, B-cells and macrophages, whereas it is not detectable in neurons.

Receptor ligands that are selective for CB1 and/or CB2 could be useful therapeutic agents in the treatment of various pathological conditions, including nausea, pain and disorders related thereto. Since far from all patients experience adequate relief of symptoms with existing drugs against these conditions, there is still a need to discover novel therapeutic compounds.

The PCT application published as WO 02/085866 discloses compounds active as CB2 agonists and their use in the management of pain. Pain categories exemplified (pages 8-9) are chronic pain, such as chronic inflammatory pain, neuropathic pain, back pain, cancer pain and visceral pain, as well as acute pain. The compounds disclosed in WO 02/085866 (cf. the $R^6$ moieties in particular) are different from those of the present invention.

Compounds of somewhat related, albeit different, structure compared to those of the present invention are disclosed e.g. in the Japanese publication JP 2002 201171 and the PCT application published as WO 91/18885.

DISCLOSURE OF THE INVENTION

The compounds of the present invention have been found to exhibit properties that render them suitable for the treatment of pain and disorders related thereto. More specifically, the present invention relates to a compound having the general formula (I):

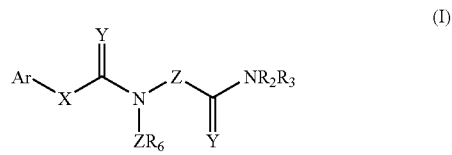

wherein
X is selected from the radicals —$NR_1$— and —$CHR_1$—;
Y is independently selected from O and S;
Z is independently selected from a $C_{1-7}$ straight or $C_{4-8}$ branched alkylene chain, a $C_{2-7}$ alkenylene chain and a part of a $C_{3-8}$ cycloalkyl or $C_{5-8}$ cykloalkenyl ring structure;
Ar is an aryl group selected from aromatic carbocyclic ring systems, five- or six-membered heteroaromatic ring systems and bicyclic heteroaromatic ring systems;
$R_1$, $R_2$ and $R_3$ are independently selected from a group of substituents (a)-(d) consisting of:
 (a) H;
 (b) $C_{1-6}$ straight or $C_{4-8}$ branched chain alkyl;
 (c) $C_{3-8}$ cycloalkyl or $C_{5-8}$ cykloalkenyl; and
 (d) $C_{2-6}$ alkenyl or alkynyl;
wherein the substituents (b)-(d) optionally have at least one substituent independently selected from a group (e)-(i) consisting of:
 (e) Ar, O—Ar or S—Ar;
 (f) OH, O-alkyl or S-alkyl, where alkyl is selected from the substituents (b)-(c);
 (g) $NR_4R_5$, where $R_4$ and $R_5$ are independently selected from the substituents (a)-(d) or optionally together form a nitrogen containing ring structure comprising from 2 to 5 carbon atoms;
 (h) NH—C(O)-alkyl, C(O)-alkyl, O—C(O)-alkyl or S—C(O)-alkyl, where alkyl is selected from the substituents (b)-(c); and
 (i) F, Cl or Br;
$R_6$ is selected from a group consisting of Ar and the substituents (a)-(c), where (b) and (c) are optionally substituted with at least one of the substituents (e)-(i);
Ar optionally has at least one substituent independently selected from the substituents (b)-(i); and tautomers, solvates, and pharmaceutically acceptable salts of said compound.

For the purposes of the present invention, the following terminology is used.

Aromatic carbocyclic ring systems includes phenyl and naphthyl.

A five-membered heteroaromatic ring system is a monocyclic aromatic ring system having five ring atoms, wherein 1, 2 or 3 ring atoms are independently selected from N, O and S. Preferred such ring systems are selected from a group consisting of thienyl, furyl, pyrrolyl, imidazolyl, thiazolyl, oxazolyl, pyrazolyl, isothiazolyl, isoxazolyl and tetrazolyl.

A six-membered heteroaromatic ring system is a monocyclic aromatic ring system having six ring atoms, wherein 1, 2 or 3 ring atoms are independently selected from N, O and S. It is preferably selected from a group consisting of pyridyl, pyrazinyl, pyrimidinyl, triazinyl and pyridazinyl.

A bicyclic heteroaromatic ring system is a ring system having two five- or six-membered heteroaromatic rings, or a phenyl and a five- or six-membered heteroaromatic ring, or a phenyl and a heterocyclyl ring, or a five- or six-membered heteroaromatic ring and a heterocyclyl ring; connected by a ring fusion, said bicyclic heteroaromatic ring system comprising 8 to 12 ring atoms, wherein 1, 2 or 3 of the ring atoms are independently selected from N, O and S. It is preferably selected from a group consisting of indole, quinoline, tetrahydroquinoline, isoquinoline, tetrahydroisoquinoline, 1,4-benzodioxan, coumarin, benzofuran, 1,2-benzisoxazole, benzothiophene, benzoxazole, benzthiazole, benzimidazole, benztriazole, pyrolizidine and quinolizidine.

A heterocyclyl or heterocyclic moiety is a saturated or partially saturated ring system having 3 to 7 ring atoms, wherein 1, 2 or 3 ring atoms are independently selected from N, O and S. Heterocyclyl moieties are preferably selected from a group consisting of aziridine, oxirane, thiirane, azetidine, oxetane, thietane, pyrrolidine, pyrroline, imidazolidine, pyrazolidine, dioxolane, tetrahydrofuranyl, piperidine, piperazine, morpholine, tetrahydropyranyl, 1,4-dioxanyl, homopiperidinyl, homopiperazinyl and hexamethylene oxide.

It deserves mentioning that e.g. also isopropyl and 2-n-butyl groups are encompassed by the expression $C_{1-6}$ straight chain alkyl, as said expression is not related to the binding site of the straight chain in question.

$C_{1-6}$ denotes having from one to six carbon atoms, including any number therebetween, and this nomenclature is used analogously herein.

Examples of pharmaceutically acceptable salts comprise acid addition salts, e.g. a salt formed by reaction with hydrohalogen acids, such as hydrochloric acid, and mineral acids, such as sulphuric acid, phosphoric acid and nitric acid, as well as aliphatic, alicyclic, aromatic or heterocyclic sulphonic or carboxylic acids, such as formic acid, acetic acid, propionic acid, succinic acid, glycolic acid, lactic acid, malic acid, tartaric, acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, toluenesulphonic acid and naphtalenesulphonic acid.

A compound (I) wherein said X is a radical —$NR_1$— is preferred. It is particularly preferred that $R_1$ is H.

It is moreover preferred that said Y in the formula (I) represents O, i.e. an oxygen atom.

The group Ar is preferably selected from phenyl and naphthyl. The naphthyl group may be either a 1- or 2-naphthyl group.

Said Z is preferably selected from —$CH_2$—, —$(CH_2)_2$—, —$(CH_2)_3$—, —$(CH_2)_5$—, —$(CH_2)_6$—, —$(CH_2)_7$— and trans-2-cyclohexylene.

Said $R_6$ is preferably selected from isopropyl, cyclopentyl, cyclohexyl, phenyl, 4-n-butylphenyl, 4-isopropylphenyl and 2-naphthyl.

It is preferred that said $R_2$ and $R_3$ are independently selected from H and 4-chlorobenzyl.

In the most preferred embodiment, said compound having the formula (I) is selected from a group consisting of:
4-[3-phenyl-1-(6-phenylhexyl)ureido]butyramide (2);
4-[1-(4-butylbenzyl)-3-phenylureido]butyramide (3);
4-[1-(4-isopropylbenzyl)-3-phenylureido]butyramide (4);
4-[1-(4-methylpentyl)-3-phenylureido]butyramide (5);
N-(4-chlorobenzyl)-4-[1-(3-cyclohexylpropyl)-3-phenyl -ureido]butyramide (6);
trans-2-[1-(3-cyclohexylpropyl)-3-phenylureido]cyclo -hexanecarboxamide (7);
4-[1-(3-cyclohexylpropyl)-3-naphthalen-2-yl-ureido]-butyramide (10);
4-[1-(2-naphthalen-2-yl-ethyl)-3-phenylureido]butyr -amide (11);
4-[1-(2-cyclohexylethyl)-3-phenylureido]butyramide (12);
4-(1-phenethyl-3-phenylureido)butyramide (13);
4-(1-benzyl-3-phenylureido)butyramide (14);
4-[1-(3-cyclopentylpropyl)-3-phenylureido]butyr -amide (15);
4-[3-phenyl-1-(5-phenylpentyl)ureido]butyramide (16); and
4-[1-(3-cyclohexylpropyl)-3-phenylureido]butyramide (17).

The number in parenthesis denotes the compound as referred to in the following.

Compound 17 is the very most preferred embodiment of the present invention. Its structure is provided below:

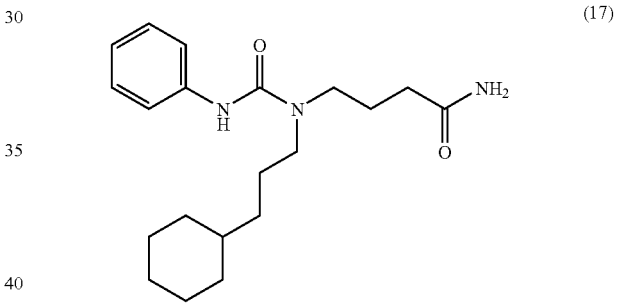

(17)

A second aspect of the present invention relates to a compound with the formula (I), wherein X is a radical —$CHR_1$—. It is preferred that said radical —$CHR_1$— is selected from —$CH_2$— and (R)—$CH(CH_3)$—. It is particularly preferred that said moieties Y, Z, Ar, $R_2$, $R_3$ and $R_6$ are embodied as set forth above.

In this second aspect of the present invention, it is most preferred that the compound is selected from a group consisting of:
(R)-4-[(3-cyclohexylpropyl)-(2-phenylpropionyl)amino]-butyramide (1);
4-[(3-cyclohexylpropyl)-(2-naphthalen-2-yl-acetyl)amino]-butyramide (8); and
8-[(3-cyclohexylpropyl)-(2-naphthalen-2-yl-acetyl)amino]-octanamide (9).

The number in parenthesis denotes the compound as referred to in the following.

Furthermore the present invention relates to a compound as set forth above for use as a pharmaceutical.

Accordingly, the present invention also relates to a pharmaceutical composition comprising a compound as set forth above as active ingredient in association with a pharmaceutically acceptable adjuvant, diluent or carrier.

The pharmaceutical composition may be adapted for oral, intravenous, topical, intraperitoneal, nasal, buccal, sublingual or subcutaneous administration or for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

It should be noted that the composition according to the present invention may optionally include two or more of the above outlined compounds.

The present pharmaceutical composition may optionally comprise e.g. at least one further additive selected from a disintegrating agent, binder, lubricant, flavoring agent, preservative, colorant and any mixture thereof. Examples of such and other additives are found in "*Handbook of Pharmaceutical Excipients*"; Ed. A. H. Kibbe, $3^{rd}$ Ed., American Pharmaceutical Association, USA and Pharmaceutical Press UK, 2000.

The present pharmaceutical composition in a solid dosage form is typically a perorally available tablet. A tablet may be manufactured by compression of a suitable granulate by procedures well established in the art. Examples of suitable tablet compressing equipment are rotary presses provided by Elizabeth-Hata International, USA, and Courtoy Nev., BE. For a comprehensive overview of pharmaceutical tablet manufacturing, see "*Tableting*" (by N. A. Armstrong) in "*Pharmaceutics—The science of dosage form design*", pp 647-668; Ed. M. E. Aulton, Churchill Livingstone, Edinburgh, London, Melbourne and New York, 1988.

In addition, the present invention relates to use of a compound as outlined above for the manufacture of a medicament for treatment of pain and disorders related thereto.

In another embodiment the invention relates to a method for treatment of pain and disorders related thereto, wherein said method comprises administering to an animal, including human, patient of a therapeutically effective amount of a compound as outlined above.

It is also anticipated that the compounds according to the present invention could be useful in the treatment of a number of other disorders, such as inflammation, autoimmune disorders, tumors, neurodegenerative disorders (especially spasticity) and gastrointestinal disorders.

The typical dosage of the compounds according to the present invention varies within a wide range and will depend on various factors such as the individual requirements of each patient and the route of administration. The dosage is generally within the range of 0.01-100 mg/kg body weight. A medical practitioner of ordinary skill in the art will be able to optimise the dosage to the circumstances at hand.

The compounds of the present invention where X is the radical —NH— and both $R_2$ and $R_3$ are H, i.e. hydrogen, can be prepared by solid phase synthesis in accordance with the following general synthetic scheme (Scheme 1). Y is O with the exemplified reagents used in the reaction steps i-viii. Z and $R_6$ are selected among the previously defined alternatives. The ball symbol used in the schemes herein is a conventional representation of a resin. It may typically be a TentaGel Rink Amide Resin.

Scheme 1

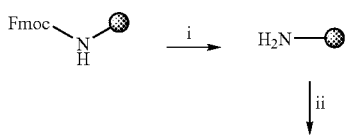

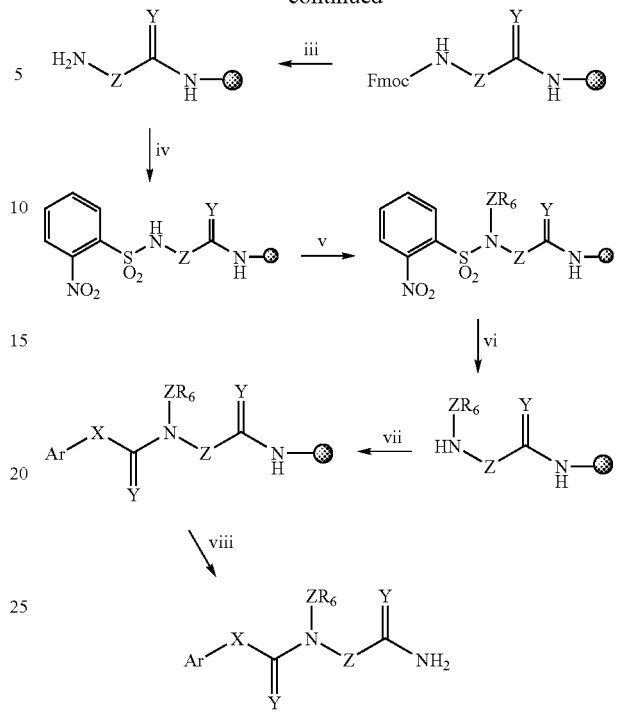

Examples of the above reagents are: i) 25% PIP/DMF; ii) Fmoc-NH-Z-$CO_2$H/HOBt/DIC, 3 eq; iii) 25% PIP/DMF; iv) o-NBS-Cl, 4 eq, collidine, 6 eq; v) $R_6$Z-OH/TPP/DIAD, 10 eq; vi) $HSCH_2CH_2OH$/DBU/DMF, 10 eq; vii) ArNCO, 10 eq; viii) TFA/$H_2O$/TIS, 96/2/2.

The following abbreviations are used:
Abu aminobutyric acid residue
BAL backbone amide linker
Boc tert-butyloxycarbonyl
DBU 1,8-diazabicyclo[5.4.0]undec-7-ene
DCM dichloromethane
DIAD diisopropyl azodicarboxylate
DIC 1,3-diisopropyl carbodiimide
DIPEA N,N-diisopropylethylamine
DME 1,2-dimethoxyethane
DMF N,N-dimethylformamide
DMSO dimethyl sulphoxide
eq equivalent
Fmoc 9-fluorenylmethyloxycarbonyl
h hour
HOBt 1-hydroxybenzotriazole
HPLC high performance liquid chromatography
MeOH methanol
min minutes
Mp melting point
MS mass spectrometry
o-NBS-Cl o-nitrobenzenesulfonyl chloride
Ph phenyl
PIP piperidine
rt room temperature
TFA trifluoroacetic acid
TIS triisopropylsilane
TPP triphenylphosphine To obtain N-monoalkylated amides, i.e. where $R_2 \neq H$ and $R_3$=H, the synthesis is performed on Rink amide resin protected with the o-NBS group (o-NBS-TentaGel-S-RAM resin). The resin is alkylated with R$_2$OH/TPP/DIAD under Mitsunobu reaction conditions. The o-NBS group is subsequently removed with a 2-mercaptoethanol/DBU/DMF cocktail. Alternatively, backbone amide linker (BAL) resin is reductively aminated with R$_2$NH$_2$. In both cases the resin bound secondary amine is subsequently acylated with Fmoc -NH-Z-CO$_2$H/DIC. The following standard reference literature provides further guidance on general experimental set up, as well as on the availability of required starting material and reagents, in the particular steps utilised in providing the compounds of the present invention:

Fukuyama, T.; Jow, C.-K.; Cheung, M. "2- and 4-Nitrobenzenesulfonamides: Exceptionally Versatile Means for Preparation of Secondary Amines and Protection of Amines" *Tetrahedron Lett.* 36:6373-6374 (1995);

Mitsunobu, O. "The Use of Diethyl Azodicarboxylate and Triphenylphosphine in Synthesis and Transformation of Natural Products" *Synthesis* 1-28 (1981);

Miller, S. C.; Scanlan, T. S. "Site-Selective N-Methylation on Solid Support" *J. Am. Chem. Soc.* 119:2301-2302 (1997);

Jensen, K. J.; Alsina, J.; Songster, M. F.; Vagner, J.; Albericio, F.; Baranay, G. "Backbone Amide Linker Strategy for Solid-Phase Synthesis of C-Terminal-Modified and Cyclic Peptides" *J. Am. Chem. Soc.* 120:5441-5452 (1998); and Rink, Hans "Solid-phase synthesis of protected peptide fragments using a trialkoxy-diphenyl-methyl ester resin" *Tetrahedron Lett.* 28:3787-3790 (1987).

The compounds 1-17 were tested in vitro for their binding to the human CB2 receptor (hCB2-R), and compound 17 was also tested in vivo as set forth in the experimental section. The following specific examples shall not be construed as a limitation of how the invention may be practised.

Experimental

Synthesis of original library (cf. steps i & ii):

Unless otherwise provided, all synthetic steps were performed at room temperature.

14 portions of Fmoc-TentaGel-S-RAM resin (0.25 mmol/g, 2.75 g each; provided from Rapp Polymere, Tübingen, Del.) were treated with a 25% solution of PIP in DMF for 30 min. The resins were thoroughly washed with DMF (2×), MeOH (2×) and DMF (2×) and subsequently acylated with 14 different Fmoc-ω-amino acids using DIC/HOBt coupling methodology with a 3-fold excess of reagents. The progress of the reaction was monitored with a conventional Kaiser's ninhydrine test.

Introduction of the o-NBS Group (cf. Steps iii & iv):

The Fmoc groups were removed by treatment with 25% PIP in DMF for 30 min and the resins were thoroughly washed as above, followed by treatment with a solution of o-NBS-Cl (4 eq) and collidine (6 eq) in DCM for 1 h. The progress of the reaction was monitored with a conventional Kaiser's ninhydrine test. Upon reaction completion the resins were suspended in DMSO/CHCl$_3$ (4:1) and the suspensions were combined. The resulting slurry was split into 16 portions (about 0.6 mmol each) and the resins were placed in 16 manual solid phase synthesis vessels and washed with dry DME.

Mitsunobu Alkylation (cf. Step v):

Each resin was then suspended in 6 ml of a solution containing 20 eq of an alcohol in dry DME. Selection criteria for the alcohols were based on results in the optimisation phase of the synthesis to provide good diversity and yields in the alkylation reactions. To each resin was then added 20 eq of a preformed TPP/DIAD complex dissolved in dry DME, and the reaction was carried out overnight. Aliquots of all 16 resins were cleaved with TFA and analysed by HPLC (Waters 600 Chromatograph) and MS (Finningan MAT Spectrometer).

Removal of the o-NBS Group (cf. Step vi):

The resins were treated with 20 eq of 1 M solutions of 2-mercaptoethanol and DBU in DMF for 1.5 h, and were washed thoroughly after the completion of the reaction.

Final Acylations (cf. Step vii):

The resins were transferred to 8 reaction blocks each having 96 wells. Each resin was then split into 48 portions and placed in the same row of blocks 1 to 4 or 5 to 8, respectively. The blocks were then arranged as shown below:

|  | acyl groups | | | | | | | |
|---|---|---|---|---|---|---|---|---|
|  | 1 | 12 | 13 | 24 | 25 | 36 | 37 | 48 |
| alcohols | 1 | | | | | | | |
|  | 8 | | | | | | | |
|  | 9 | | | | | | | |
|  | 16 | | | | | | | |

Columns 1 to 4 were acylated with Fmoc-amino acids, columns 5 to 20 were acylated with Boc-amino acids, and columns 21-37 with carboxylic acids using 15 eq of an acid and 15 eq of DIC. Column 38 was treated with 15 eq of acetic anhydride/DIPEA. For the synthesis of the sulphonamides (columns 39-43) an appropriate sulphonyl chloride (15 eq) and DIPEA (22.5 eq) were used. Finally the ureas (columns 44-48) were formed using an appropriate isocyanate (15 eq) in DMF. All the reactions were carried out overnight at rt. The completion of the reactions was confirmed (one test per column) with a conventional chloranil test. The Fmoc groups (columns 1 to 4) were then removed by treatment with 25% PIP/DMF, after which the entire library was washed out with DMF, MeOH and DCM followed by drying in vacuo.

Cleavage (cf. Step viii):

The compounds were cleaved from the resin by treatment with 0.5% H$_2$O in TFA overnight. The resin was removed by filtration and the filtrates were collected in 8 plates each having 96 wells. The solvent was removed by evaporation in a conventional Savanth centrifuge. The library was reconstituted in MeOH/H$_2$O (1:1, v/v), and the solvents were evaporated in a Savanth centrifuge. The final product was an original library consisting of 768 mixtures each containing 14 compounds.

Synthesis of Deconvolution Library:

By screening of the original library against hCB2-R, 12 active wells were identified. Since each well contained 14 compounds the deconvolution library needed to consist of 168 discrete compounds. The deconvolution library and two subsequent optimisation libraries were obtained according to the protocol for the original library, albeit the mix and split steps were omitted.

Synthesis of 4-[1-(3-cyclohexylpropyl)-3-phenyl-ureido] butyramide (compound 17):

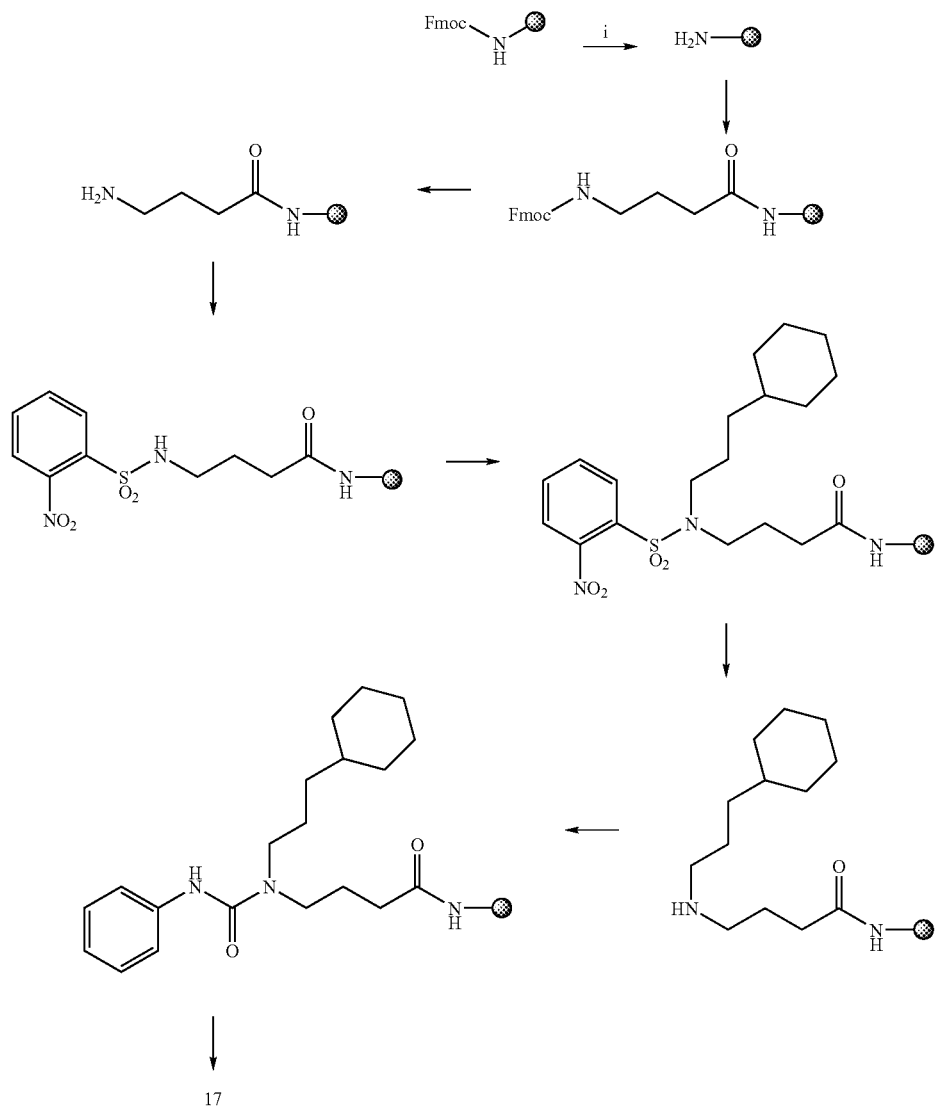

Scheme 2

17

10 g of Fmoc-TentaGel-S-RAM resin (0.25 mmol/g, 2.5 mmol) was treated with 25% PIP in DMF for 30 min. The resin was washed with DMF (2×), MeOH (2×) and DMF (2×) and subsequently acylated with Fmoc-γ-Abu-OH/DIC/HOBt (3 eq) in DMF. The completeness of the reaction was assessed with Kaiser's ninhydrine test. The Fmoc group was removed followed by resin washing as described above. The o-NBS group was introduced by treatment with o-NBS-Cl (4 eq)/collidine (6 eq) in DCM for 1 h at rt. The resin was then suspended in dry DME (15 ml) and 3-cyclohexyl-1-propanol (3.8 ml, 25 mmol, 10 eq) was added. The TPP/DIAD complex was preformed at 0° C. by dissolving TPP (6.55 g, 25 mmol, 10 eq) in dry DME (30 ml) and adding DIAD (4.92 ml, 25 mmol, 10 eq). The complex was then added to the suspension and the reaction was carried out overnight. An aliquot of the resin was cleaved and analysed by HPLC (column: Vydac C18, 5 μp, 250×4.6 mm; solvents: A-0.1% TFA (aq), B-80% CH$_3$CN/0.1% TFA (aq); a linear gradient of B was used). The content of the non-alkylated substrate was below 2%. The o-NBS group was subsequently removed by treatment with 1 M 2-mercaptoethanol/DBU in DMF (25 ml) for 1 h (2×). The resin was then treated with PhNCO (10.9 ml, 25 mmol, 10 eq) in DMF-for 4 h. The completeness of the reaction was confirmed by a negative chloranil test. The compound was cleaved from the resin by treatment with TFA/TIS/H$_2$O 96/2/2 (100 ml) for 1.5 h at rt. The resin was filtered off and the solvents were evaporated. The crude product was purified by preparative HPLC. The fractions containing the pure compound were combined and lyophilised. The obtained product was treated with isopropyl ether, whereby crystalline compound was provided. Yield: 442.8 mg (51%, 1.28 mmol); Mp. 104-106° C.; MS (ion spray): [M+H]$^+$ expected 346.2, observed 346.2; $^1$H NMR (500 MHz, CDCl$_3$) data was consistent with the structure of compound 17.

The biological assays used were essentially set up as described in Munro, S., Thomas, K. L., Abu-Shaar, M. in "Molecular characterisation of a peripheral receptor for cannabinoids" *Nature* 365:61-65 (1993) and Kim, S. H. and Chung, J. M. in "An experimental model for peripheral neuropathy produced by segmental spinal nerve ligation in the rat" *Pain* 50:355-363 (1992).

In vitro Assays:

Monoclonal HEK cell lines with stable expression of the human CB1 receptor and CHO-K1 cell lines with stable expression of hCB2-R were established. The CB binding assays were performed with membranes prepared from these cell lines. The CB2 ligand binding mixture contains 0.3-0.5 nM [$^3$H]-CP55940, 7 μg of CB2 membranes and the test compounds in a concentration range of from $1.0 \times 10^{-4}$ to $1.0 \times 10^{-12}$ M. The assay buffer comprises 50 mM Tris-HCl (pH 7.4), 5 MM MgCl$_2$, 2.5 mM EDTA and 5 mg/ml fatty acid-free bovine serum albumin. The binding mixtures are incubated for 2 h at 30° C. and terminated by rapid filtration (Brandel 96 well cell harvester) over 934AH filters (Whatman) followed by 6 washes with ice-cold binding buffer. The filters are dried and [$^3$H]-CP55940 bound radioactivity is determined by liquid scintillation counting. Non-specific binding is determined in the presence of 10 μM CP55940. The binding data is analysed with the program GraphPad Prism (provided by GraphPad Software, San Diego, Calif., USA). The K$_i$ values presented in table 1 were obtained.

TABLE 1

Binding constants (K$_i$) to hCB2-R.

| Compound | K$_i$ (μM) |
|---|---|
| 1 | 2.9 |
| 2 | 0.45 |
| 3 | 0.12 |
| 4 | 0.78 |
| 5 | 1.1 |
| 6 | 2.2 |
| 7 | 1.5 |
| 8 | 2.7 |
| 9 | 15 |
| 10 | 1 |
| 11 | 0.77 |
| 12 | 0.41 |
| 13 | 0.45 |
| 14 | 0.84 |
| 15 | 0.21 |
| 16 | 0.13 |
| 17 | 0.11 |

In vivo Assays:

Inflammatory (Formalin flinch test) and chronic pain (L5/L6 nerve ligation injury) models were used as assays in both rats and mice.

Formalin flinch test:

Animals are habituated to the their local environment for about 30 min prior to testing. The formalin test is carried out in a 30×30×30 cm chamber with the front and bottom of the chambers made of clear plexiglass. Mirrors are placed at a 45° angle under the chambers in order to have an un-obstructive view of the paws. Animals are restrained manually and 2% formalin (aq) is injected subcutaneously into the planar surface of the left paw with a 30 gauge needle. The numbers of paw flinches are then recorded in 5 min intervals from the time of injection for a 60 min period. Elevations of the paw, licking and biting of the injected paw were counted as "flinches". The tonic or "first phase" of the nociceptive response peaked at 5 min after formalin injection and the inflammatory or "second phase" peaked at 30 min after formalin injection. The number of flinches in the first 10 min were representative of the tonic phase and the number of flinches from 10 min until 60 min were representative of the inflammatory phase. Antinociception for both phase I and phase II was calculated as follows:

% antinociception=100×(# of flinches in control animal−# of flinches in drug treated animal)/(# of flinches in control animal)

Potency (A$_{50}$) is calculated from the full dose response curve for both phase I and phase II. The results are shown in table 2:

TABLE 2

A$_{50}$ of compound 17 in rat models of inflammatory and chronic pain

| | WIN-55, 212-2 | Compound 17 | |
|---|---|---|---|
| | i. paw | i. paw | i.p. |
| Formalin Phase I | 12 mg/paw | <10 mg/paw | <0.01 mg/kg |
| Formalin Phase II | 25 mg/paw | 28 mg/paw | 0.01 mg/kg |
| L5/L6 anti-allodynia | | <30 mg/paw | |
| L5/L6 anti-hyperalgesia | | <30 mg/paw | |

WIN-55, 212-2 is a non-selective cannabinoid agonist widely used as a reference compound in both in vitro and in vivo assays. It was first described by T. E. D'Ambra et al. in *J. Med. Chem.* 35:124-135 (1992).

L5/L6 Nerve Ligation Injury:

Nerve ligation injury was performed according to the method described previously (Kim and Chung). This methodology produces signs of tactile allodynia and thermal hyperalgesia. Rats were anesthetized with halothane and the L5 and L6 spinal nerves were exposed, carefully isolated, and tightly ligated with 4-0 silk suture distal to the dorsal root ganglia (DRG). After ensuring homeostatic stability the wounds were sutured, and the animals were allowed to recover in individual cages. Sham-operated rats were prepared in an identical fashion except that the L5 and L6 spinal nerves were not ligated. Compound 17 was tested in rats after L5/L6 nerve ligation. Compound administration was directly into the hind paw (i.paw) or into the peritoneal cavity (i.p.).

In the evaluation of the tactile allodynia, the paw withdrawal threshold was determined in response to probing with calibrated von Frey filaments. The rats were kept in suspended cages with wire mesh floors and the von Frey filaments were applied perpendicularly to the planar surface of the paw of the rat until it bent slightly, and was held for 3 to 6 s, or until the paw is withdrawn. A positive response was indicated by a sharp withdrawal of the paw. The 50% paw withdrawal threshold was determined by the nonparametric method. Data were converted to percentage of antiallodynia by the formula:

% antiallodynia=100×(test value−control value)/(15 g−control value)

Compound 17 resulted in a 90% antiallodynic effect upon administration of 100 μg (in 50 μl) into the paw. It also resulted in a 100% antihyperalgesic response to the thermal testing in the L5/L6 spinal nerve ligation animals after administration of 30 μg (in 50 μl) into the paw.

The biological results as set forth above establish that the present compounds of formula (I) are suitable for the treatment of pain and disorders related thereto. They would hence also be suitable for the treatment of inflammatory disorders.

All of the literature referred to is to be regarded as an integral part of the present writ.

The invention claimed is:

1. A compound having the formula:

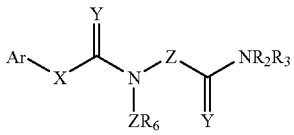

wherein

Z' is —(CH$_2$)$_3$— or cyclohexyl;

Z is selected from a C$_{1-7}$ straight or branched chain alkyl, a C$_{4-8}$ branched alkylene chain, and a C$_{2-7}$ alkenylene chain;

Ar is an aryl group independently selected from an aromatic carbocyclic ring system, a five- or six-membered heteroaromatic ring system and a bicyclic heteroaromatic ring system;

R$_3$ is selected from a group of substituents (a)-(d) consisting of:
(a) H;
(b) C$_{1-6}$ straight chain or C$_{4-8}$ branched chain alkyl;
(c) C$_{3-8}$ cycloalkyl or C$_{5-8}$ cycloalkenyl; and
(d) C$_{2-6}$ alkenyl or alkynyl;

wherein the substituents (b)-(d) optionally have at least one substituent independently selected from a group (e)-(i) consisting of:
(e) Ar, —O—Ar or —S—Ar;
(f) OH, O-alkyl or S-alkyl, where alkyl is selected from the substituents (b)-(c);
(g) —NR$_4$R$_5$, where R$_4$ and R$_5$ are independently selected from the substituents (a)-(d) or optionally together form a nitrogen containing ring structure comprising from 2 to 5 carbon atoms;
(h) —NH—C(O)-alkyl, —C(O)-alkyl, —O—C(O)-alkyl or —S—C(O)-alkyl, where alkyl is selected from the substituents (b)-(c); and
(i) F, Cl or Br;

R$_6$ is selected from a group consisting of Ar and the substituents (a)-(c), where (b) and (c) are optionally substituted with at least one of the substituents (e)-(i);

Ar optionally has at least one substituent independently selected from the substituents (b)-(i); or a tautomer, solvate or pharmaceutically acceptable salt of said compound.

2. The compound or a tautomer, solvate or pharmaceutically acceptable salt thereof according to claim 1, wherein Ar is selected from phenyl and naphthyl.

3. The compound or a tautomer, solvate or pharmaceutically acceptable salt thereof according to claim 1, wherein Z is selected from —CH$_2$—, —(CH$_2$)$_2$—, —(CH$_2$)$_3$—, —(CH$_2$)$_4$—, —(CH$_2$)$_5$—, —(CH$_2$)$_6$—, and —(CH$_2$).

4. The compound or a tautomer, solvate or pharmaceutically acceptable salt thereof according to claim 1, wherein R$_6$ is selected from isopropyl, cyclopentyl, cyclohexyl, phenyl, 4-n-butylphenyl, 4-isopropylphenyl and 2-naphthyl.

5. The compound or a tautomer, solvate or pharmaceutically acceptable salt thereof according to claim 1, wherein R$_2$ and R$_3$ are independently selected from H and 4-chlorobenzyl.

6. The compound or a tautomer, solvate or pharmaceutically acceptable salt thereof according to claim 1, wherein the compound is selected from a group consisting of:
4-[3-phenyl-1-(6-phenylhexyl)ureido]butyramide;
4-[1-(4-butylbenzyl)-3-phenylureido]butyramide;
4-[1-(4-isopropylbenzyl)-3-phenylureido]butyramide;
4-[1-(4-methylpentyl)-3-phenylureido]butyramide;
N-(4-chlorobenzyl)-4-[1-(3-cyclohexylpropyl)-3-phenylureido]butyramide;
trans-2-[1-(3-cyclohexylpropyl)-3-phenylurei do]cyclohexanecarboxamide;
4-[1-(3-cyclohexylpropyl)-3-naphthalen-2-yl-ureido]butyramide;
4-[1-(2-naphthalen-2-yl-ethyl)-3-phenylureido]butyramide;
4-[1-(2-cyclohexylethyl)-3-phenylureido]butyramide;
4-(1-phenethyl-3-phenylureido)butyramide;
4-(1-benzyl-3-phenylureido)butyramide;
4-[1-(3-cyclopentylpropyl)-3-phenylureido]butyramide;
4-[3-phenyl-1-(5-phenylpentyl)ureido]butyramide; and
4-[I-(3-cyclohexylpropyl)-3-phenylureido]butyramide.

7. A pharmaceutical composition comprising the compound or a tautomer, solvate or pharmaceutically acceptable salt thereof according to claim 1 and a pharmaceutically acceptable adjuvant, diluent or carrier.

8. The compound according to claim 2, wherein Ar is phenyl.

9. The compound according to claim 3, wherein Ar is phenyl

10. The compound according to claim 3, wherein Z is a C$_{2-7}$ straight chain alkyl.

11. The compound according to claim 3, wherein Z is selected from the group consisting of —(CH$_2$)—, —(CH$_2$)$_2$—, —(CH$_2$)$_3$— and —(CH$_2$)$_5$—.

12. The compound according to claim 3, wherein Z is —(CH$_2$)—.

13. The compound according to claim 2, wherein R$_6$ is C$_{3-8}$ cycloalkyl.

14. The compound according to claim 3, wherein R$_6$ is C$_{3-8}$ cycloalkyl.

15. The compound according to claim 14, wherein R$_6$ is cyclohexyl.

16. The compound according to claim 2, wherein R$_3$ is H, C$_{1-6}$ straight or C$_{4-8}$ branched chain alkyl.

17. The compound according to claim 3, wherein R$_3$ is H, C$_{1-6}$ straight chain or C$_{4-8}$ branched chain alkyl.

18. The compound according to claim 17, wherein R$_3$ is H.

19. The compound according to claim 9, wherein R$_6$ is C$_{3-8}$ cycloalkyl.

20. The compound according to claim 19, wherein R$_6$ is cyclohexyl.

* * * * *

UNITED STATES PATENT AND TRADEMARK OFFICE
CERTIFICATE OF CORRECTION

PATENT NO. : 7,504,538 B2
APPLICATION NO. : 10/575976
DATED : March 17, 2009
INVENTOR(S) : Chi-Ping Chang et al.

It is certified that error appears in the above-identified patent and that said Letters Patent is hereby corrected as shown below:

Col. 13 in claim 1 the formula should appear as follows:

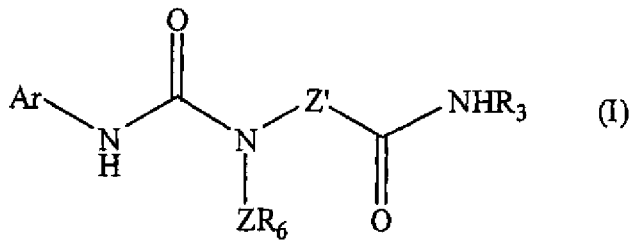

Col. 13 in claim 3, line 54, replace "and $-(CH_2)$ ." with "and $-(CH_2)_7$."

Signed and Sealed this

Twenty-first Day of April, 2009

JOHN DOLL
*Acting Director of the United States Patent and Trademark Office*